United States Patent
Riley (10) Patent No.: US 8,122,995 B1
(45) Date of Patent: Feb. 28, 2012

(54) EAR-MOUNTED LENTICULAR ACOUSTIC REFLECTOR

(75) Inventor: Michael D. Riley, Glendale, AZ (US)

(73) Assignee: Michael D. Riley, Glendale, AZ (US)

( * ) Notice: Subject to any disclaimer, the term of this patent is extended or adjusted under 35 U.S.C. 154(b) by 0 days.

(21) Appl. No.: 12/954,914

(22) Filed: Nov. 29, 2010

(51) Int. Cl.
*H04R 25/00* (2006.01)

(52) U.S. Cl. .................... 181/129; 181/130; 181/135

(58) Field of Classification Search .............. 181/129, 181/130, 135
See application file for complete search history.

(56) References Cited

U.S. PATENT DOCUMENTS

| | | | | |
|---|---|---|---|---|
| 4,768,613 A | * | 9/1988 | Brown | 181/136 |
| 4,997,056 A | * | 3/1991 | Riley | 181/136 |
| 5,020,629 A | * | 6/1991 | Edmundson et al. | 181/136 |
| 5,749,099 A | * | 5/1998 | Voorhees | 2/209 |
| 5,965,850 A | * | 10/1999 | Fraser | 181/129 |
| 7,028,343 B1 | * | 4/2006 | Watson | 2/209 |
| 7,117,546 B2 | * | 10/2006 | Goulding | 2/423 |
| 2004/0237175 A1 | * | 12/2004 | Carrafield et al. | 2/423 |
| 2006/0151236 A1 | * | 7/2006 | McCool | 181/129 |

\* cited by examiner

*Primary Examiner* — Forrest M Phillips (57) ABSTRACT

The present invention pertains to an ear-mountable, paraboloid-shaped reflective acoustic lens which can be used to enhance a user's perception of the sounds from a source the user faces. The lens mechanically collects and naturally amplifies the airborne acoustic information from the sound source. The lens uses both the wearer's external ear as well as the interior face of an acoustic lens to coherently reflect increased amounts of sound from the source into the ear canal of a user who wears the lightweight, deformable lens. All sections of the lens meet the head of the user at an obtuse angle. The lens is held in place around the user's ear by the inward pressure of the lens pushing against the outside of the user's pinna. Adherence of the device to the ear of the wearer can be increased by an adhesive strip on the interior face of the lens.

3 Claims, 8 Drawing Sheets

EAR-MOUNTED LENTICULAR ACOUSTIC REFLECTOR

TECHNICAL FIELD

The present invention pertains to an ear-mountable reflective acoustic lens with a shape that approximates an oblate spherical-section lune or diangle paraboloid which can be used to enhance a user's perception of the sounds generated by a sound source which the user faces. The invention's lens does so by mechanically collecting and more naturally amplifying the airborne acoustic information transmitted in the user's direction from the sound source. The lens uses both a larger portion of the interior surface of the wearer's external ear (pinna or auricle and concha) as well as the interior face of an acoustic lens to intercept and coherently reflect increased amounts of sound waves radiated by the sound source into the ear canal of a user who wears the invention's lightweight and deformable lens. The base of all sections of the lens intersects the head of the user at an obtuse angle at all points. The lens is held firmly but comfortably in place around either one or both of the user's ear or ears as a result of the inward pressure of the interior face of the lens pushing against the outside surface of the user's pinna. Fixed-position adherence of the device to the ear of the wearer can be optionally increased by means of affixing an adhesive strip to the interior face of the lens.

BACKGROUND OF THE INVENTION

1. Field of the Invention

The present invention relates generally to novel improvements in devices for mechanically and coherently amplifying the amount of sound wave radiation that is perceived by those with normal, unaided human ears. More particularly, it relates to such devices for mechanically directing these sound waves into one or both of the ears of a user in a manner that is both comfortable and that effectively recreates a phase-coherent, amplified image of the source of those sounds that the user faces. This invention also reduces the likelihood that onlookers will notice the device that produces this amplification when it is worn by a user. While prior art describes devices that can also reflectively increase the amount of sound received by the ears of users, none can perform this function with the unique combination of acoustic fidelity, comfort, reduced self-consciousness, and selectivity of the present invention.

Like other circumaurally-mounted oblate spherical lune or diangle-shaped paraboloid acoustic lenses, the present invention's roughly two-inch-diameter acoustic reflector effectively doubles the length of the user's ear canal by extending it. This increase helps to improve the user's perception of all sounds with a frequency of over 1.5 kilohertz, by cutting the resonant frequency of the ear canal in half. This increases the perceptibility of important frequencies in human speech (from 500 Hertz to 8 kilohertz) as well as musical fundamental notes as well as overtones. Further improvement to the volumes and coherence of the sounds amplified by the user's pinna as well as by the acoustic lens of the device are produced by using an obtuse angle at all points formed by the intersection of the transverse axis arcs of all sections of the lens at the line of its intersection with the head of the user.

Additionally and uniquely, the shape of the interior surface of the pliable material from which the invention is fabricated pushes against the top, rear, and bottom of the exterior of the pinna of the user's ear in order to move its rear face forward to form an obtuse angle to the head, and to hold the pinna fixed outward in this position. This increases the ability of the front, inner face of the user's pinna as well as a portion of the concha to reflect and focus sound radiated from sources in front of the user into the ear canal, as well as reflecting more focused sound from the inner face of the invention's lens. Since the pinna is known to serve as a directional collector and funnel for sound (for example, see http://en.wikibooks.org/wiki/Sensory_Neuroscience:_Hearing_and_speech/Outer_&_middle_ear/pinna), this repositioning improves the user's ability to identify the specific spatial positions of sound sources faced by the user. As noted on page 464 of the book *Listening*, by Stephen Handel (The MIT Press, 1989), "the pinna aids in front-to-back localization . . . [and its shape] creates a frequency filter so that as a sound source moves vertically from below the head to above the head, different frequency bands are accentuated and diminished. These changes provide localization information for elevation."

2. Description of the Prior Art

The present invention's inventor noted the following in his previous patent covering a somewhat similar application of paraboloid acoustic lenses (U.S. Pat. No. 4,997,056):

"Researchers in related electroacoustic fields have identified such phenomena as sound wave phase incoherence and frequency group delays as causes for reduced information delivery by sound waves. Group delay causes a loss of natural realism to the perception of sounds, especially transients; in terms of measurements, group delay is plotted as the slope, or first derivative function of, phase shift versus frequency, showing the amount of time delay that is undergone by signal components in different segments of the frequency spectrum perceptible to humans. "Folded exponential horn" systems, such as described in Deutsches Reich Patentschrift Nr. 344526, issued Nov. 23, 1921 and U.S. Pat. No. 3,938, 616, issued Feb. 17, 1976 to Brownfield, can cause sound waves to acquire these kinds of distortions, by causing excessive reflections and resonances within the amplifying device itself.

"Testing of active transducers (stereo headphones) used in close proximity to the ear has revealed that " . . . sound pressure produced at the eardrum is critically dependant on the wave properties of the earphone and the external ear. The geometry of the cavities coupling the earphone to the ear drum, which is affected by such factors as the positioning of the earphone on the head of the listener, becomes the most critical issue [emphasis added]. These wave effects become important . . . at frequencies above about 2,000 Hertz . . . (sound pressures at the eardrum are) critically dependant on the geometry of the earphone and ear and the exact positioning of the earphone . . . ."; from a letter by Zwislocki, Kruger, Miller, Niemoeller, Shaw and Studebaker appearing in the April, 1988 issue of the Journal of the Acoustical Society of America.

"A variety of additional hearing assistance devices and related structures are known in the art, which do not deal with the perceptible effects of the geometry of the invented device in relationship to the ear of the user. For example, hearing assistance devices including a cup configured for positioning behind and extending outward beyond the user's ear are shown in the following issued U.S. Pat. Nos. 1,708,257, issued Apr. 9, 1929 to Campbell; 1,820,107, issued Aug. 25, 1931 to Agee; 2,537,201, issued Jan. 9, 1951 to Amfitheatrof; U.S. Pat. No. 4,574,912, issued Mar. 11, 1986 to Fuss et al. Somewhat related structures in combination With eyeglasses are disclosed in U.S. Pat. No. 1,621,629, issued Mar. 27, 1927 to Dawson and U.S. Pat. No. 3,943,925, issued Mar. 16, 1976 to Leight. None of these prior art devices overcome the problems with such devices discussed above."

What was implicit in the above statements but not noted in the claims cited for any patent before or since (including U.S. Pat. No. 4,997,056) is the need to form the pinna of the human ear into a more effective acoustic lens shape in order to enable the ear to naturally collect more radiated sounds. The use of the tissue of the ear for this purpose is inherently superior to the use of any other material, as will be noted by using one's hand cupped around one's ear, in a variety of positions and shapes, as a means of determining the optimum form for such a sound collector and concentrator. Given the characteristic shape of most human ears, a parabolic curve that forms an oblate lune or diangle portion of a sphere is likely to prove to be the most effective and comfortable shape for this novel acoustically reflective lens.

Subsequent patents of several devices designed to increase the perceived volume of sound sources, such as U.S. Pat. Nos. 5,345,512, 5,965,850, 6,082,486, and 6,237,714, all suggest the use of headband mountings to hold reflectors or lenses in place behind both ears of a user. U.S. Pat. No. 5,965,850 does call for using the headband's reflectors to position the user's pinna forward, but it does not use the reflector to induce an acoustic lens-shaped configuration in the positioning of the ear.

One other (apparently unpatented) product called "Serious Listeners" was briefly marketed in the mid-Nineties. This device used a pair of softly pliable, foldable leather reflectors to permit the user to use the product on one ear at a time; however, it did not provide lenticular accuracy to its reflections, nor did it permit the user to prop the pinna forward in optimum listening position.

BRIEF SUMMARY OF THE INVENTION

Accordingly, it is an object of this invention to provide a non-electronic acoustic device that mechanically intersects more sound wave radiation than can the human ear alone, and that reflects and concentrates those sound waves into either one or both of the user's ear or ears in a focused manner that better preserves the phase-coherency and accurate sonic image relationships in these sound waves, thus permitting the user to comfortably perceive a more natural and intelligible amplification of only those sounds to which the user wishes to direct his or her attention.

Another object of this invention is to provide means to reshape the pinna of the user's external ear into a form that is capable of intersecting, concentrating and reflecting more of the sounds radiated from sound sources that the user chooses to face.

Yet another object is to provide this coherent amplification in a manner that will reduce the likelihood of objectionable ridicule being addressed to users, ridicule which larger and more noticeable sizes for these acoustic devices can produce from those who observe users of these devices. Reduced risk of ridicule can diminish or even eliminate the unpleasant sense of self-consciousness that users of other such devices may experience.

Another object is to provide this amplification with a higher degree of selectivity, so that not only can the user simply move his or her head to face the sound source of interest in order to choose the sounds to be amplified, but also so that the user can elect to employ this amplification on only one ear at a time, specifically whichever ear the user may regard as his or her "bad ear."

An additional object is to permit the user to quickly and conveniently put on and then remove these reflectors and to store them in a nested configuration in a small volume, such as in a pocket or purse.

A further object is to permit these light-weight acoustic reflectors to be firmly but comfortably held in the optimum position on the user's ear by means of the shape molded into the pliable film material from which the device is fabricated, as well as an optional adhesive strip to be placed on the interior face of the reflector.

A further object is to provide clear visual cues to the user of a reflector that any protective strip of material placed over the optional adhesive strip that may be used to preserve its adhesive qualities before use needs to be removed in order to assure the best adherence of the reflector to the pinna of the user.

A still further object is to permit the amplifying device to block spurious sound waves radiated by sound sources not of interest to the user, specifically those sounds originating to the user's sides and rear, and to thereby reduce the perceived volume of those unwanted sounds that are still conducted into the ear canal of the user.

A still further object is to permit the device to be used for a variety of functions, including two functions simultaneously—one function for each ear.

A still further object is to provide all of these benefits in a manner that permits the device to be produced, packaged and sold without prohibitive cost and to therefore be profitably sold at a relatively inexpensive price.

Further objects of the invention will be identified as the description proceeds. The attainment of these and related objects may be achieved through use of the novel acoustic device that mechanically intercepts and reflects into an ear canal of a user a greater amount of frontally generated sound waves herein disclosed.

The attainment of the foregoing and related objects, advantages and features of the invention should be more readily apparent to those skilled in the art, after review of the following more detailed description of the invention, taken together with the drawings, in which:

DETAILED DESCRIPTION OF THE INVENTION

Figure 1:
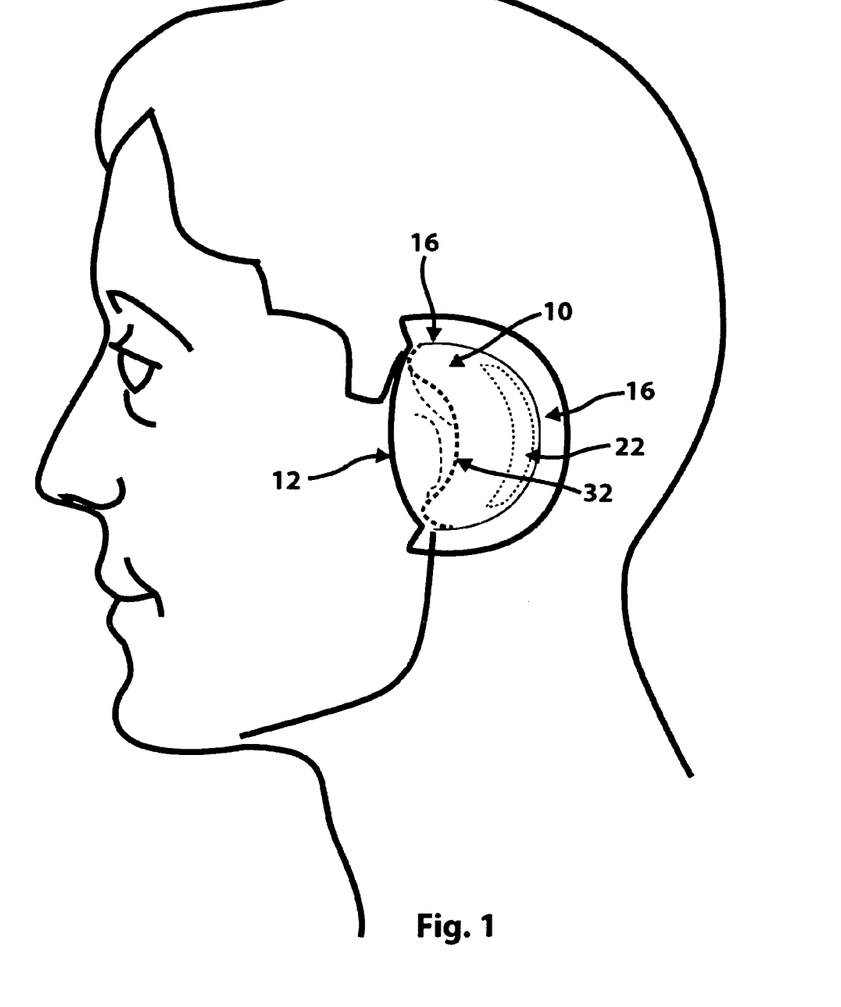
FIG. 1 is a view of the invention in use on the user's left ear, as seen with the user facing to the left and the observer facing the user's left side.
Figure 2:
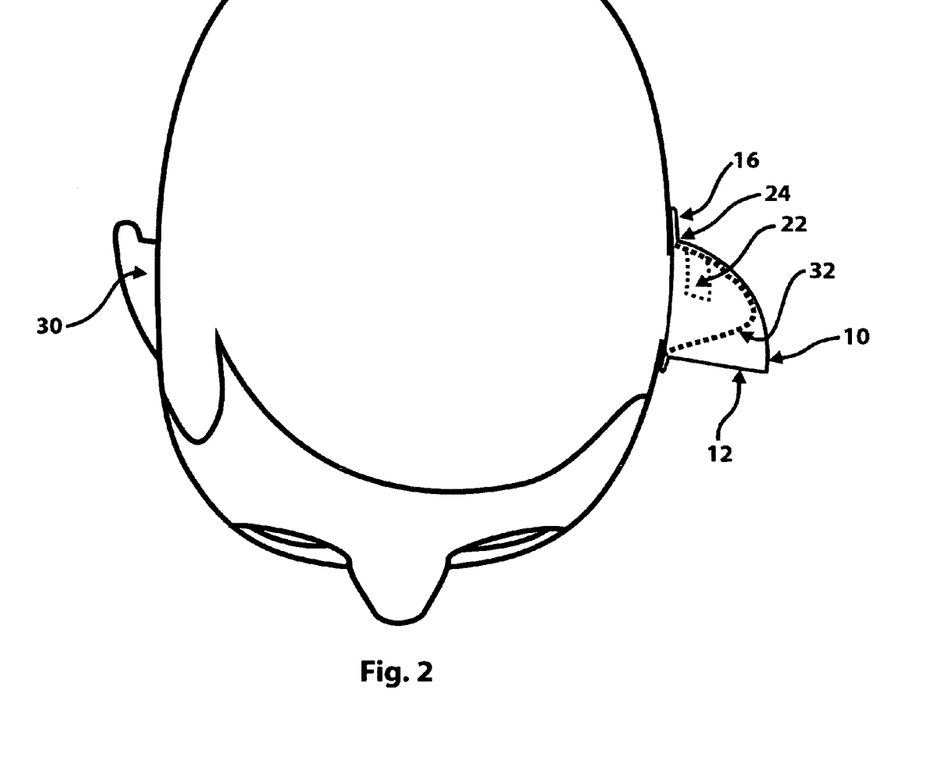
FIG. 2 is a view of the invention in use on the listener's left ear, as seen looking down from above the listener's head from above, with the listener facing downward in the drawing.
Figure 3:
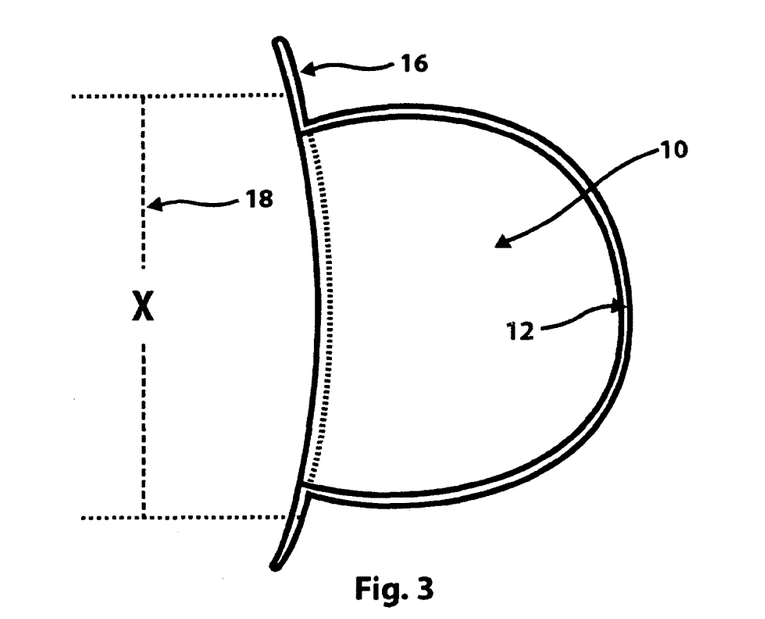
FIG. 3 is a view of the front face of the invention positioned as it would appear when worn on a user's left ear when the user is facing the observer, but without being worn by any user as depicted. The version shown uses only the force of the inward pressure generated by the shape of the invention's elastically deformable, curved inner surface to hold the invention in place.
Figure 4:
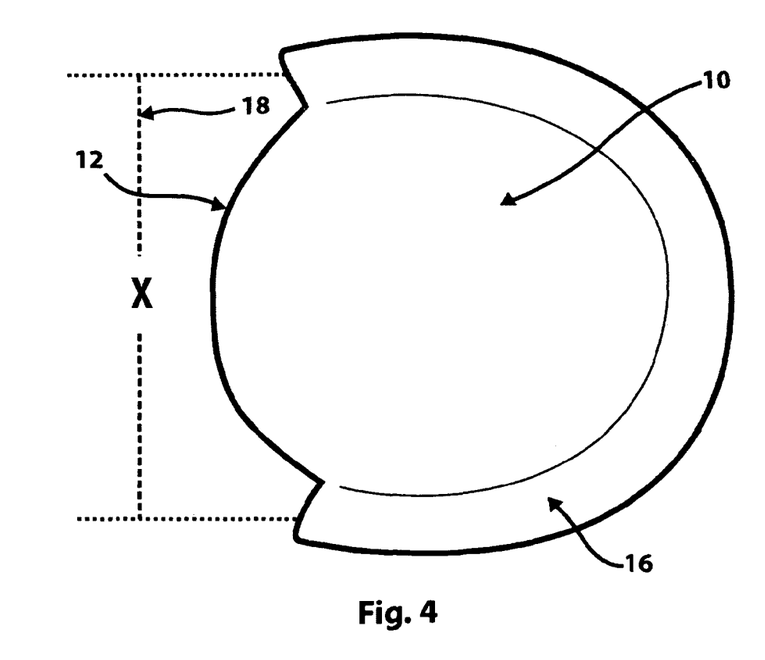
FIG. 4 as in FIG. 3 is a view of the outer side of the invention positioned as it would be when worn on the user's left ear when the user is facing to the left as in FIG. 1, but without being worn in the view shown here, and again as in FIG. 3 with the capability of being held in place only by pressure created by the shape of the invention's elastically deformable, curved inner surface.
Figure 5:
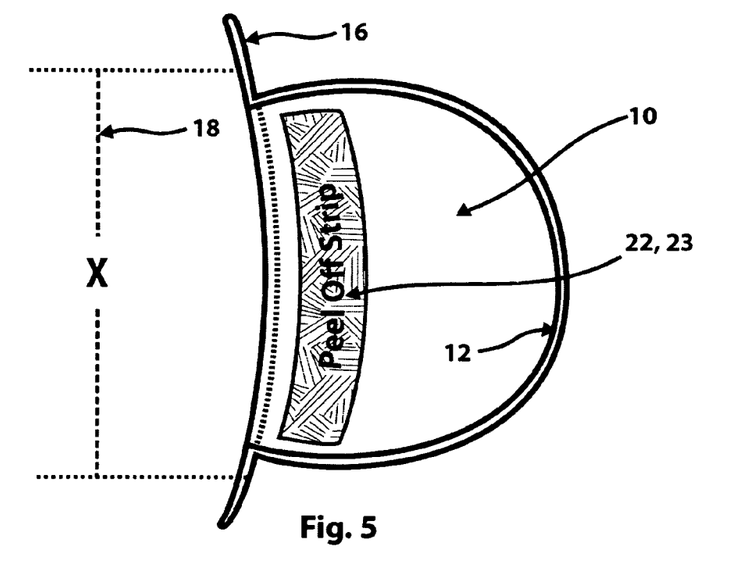
FIG. 5 is a view of the front face of the invention positioned as it would be when worn on the user's left ear when the user is facing the observer as in FIG. 1 and FIG. 3, without being worn in the view shown here, and with the additional capability of being held in place by an adhesive strip affixed to the rear of the inner surface of the invention.
Figure 6:
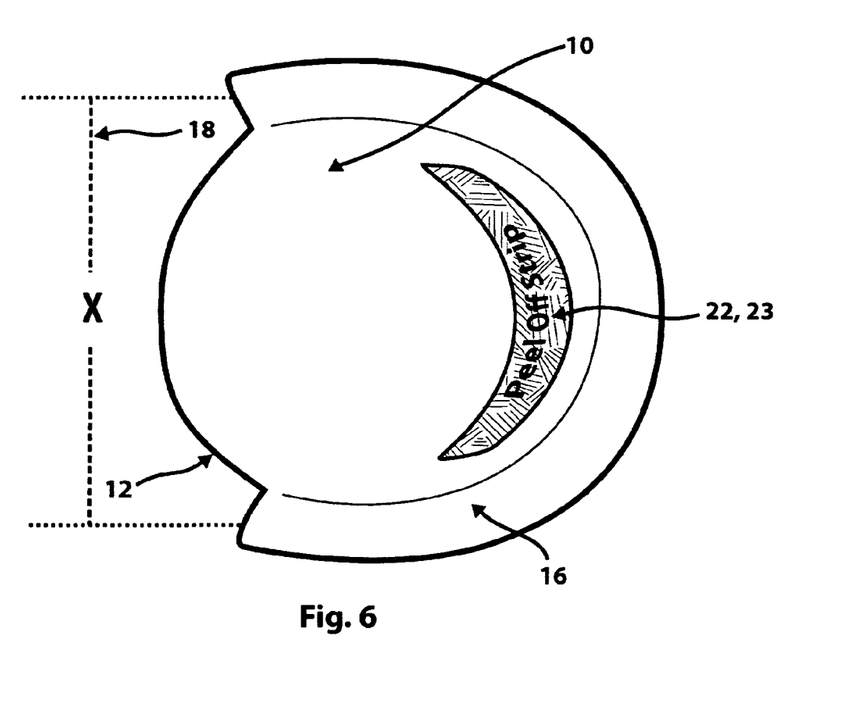
FIG. 6 as in FIG. 4 is a view of the outer face of the invention positioned as it would be when worn on the user's left ear when the user is facing to the left, here depicted as without being worn by any user and as in FIG. 5 with an adhesive strip affixed to the inner rear surface of the invention.
Figure 7:
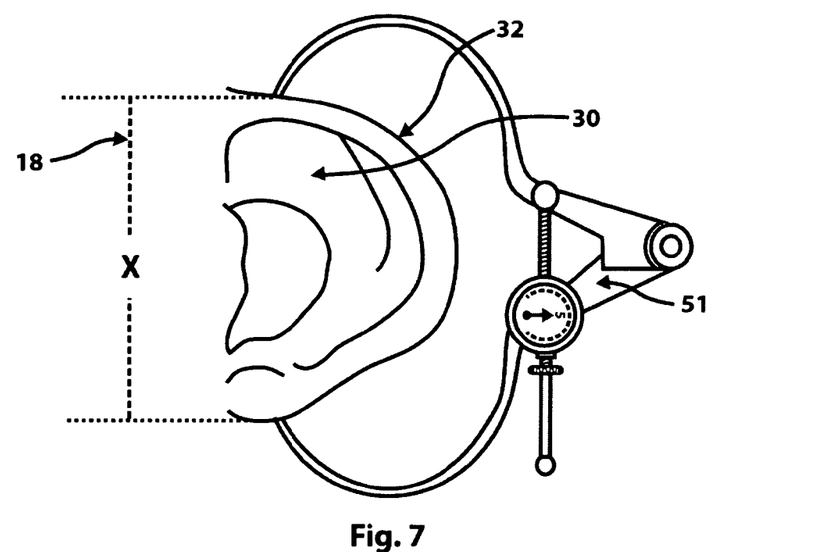
FIG. 7 is a side view of a person's left ear being measured by pressure-reading calipers to determine the pressure required to produce a specified length ("X") from the topmost point of the ear's pinna next to its junction with the person's head, to the same position on the pinna's bottom.
Figure 8:
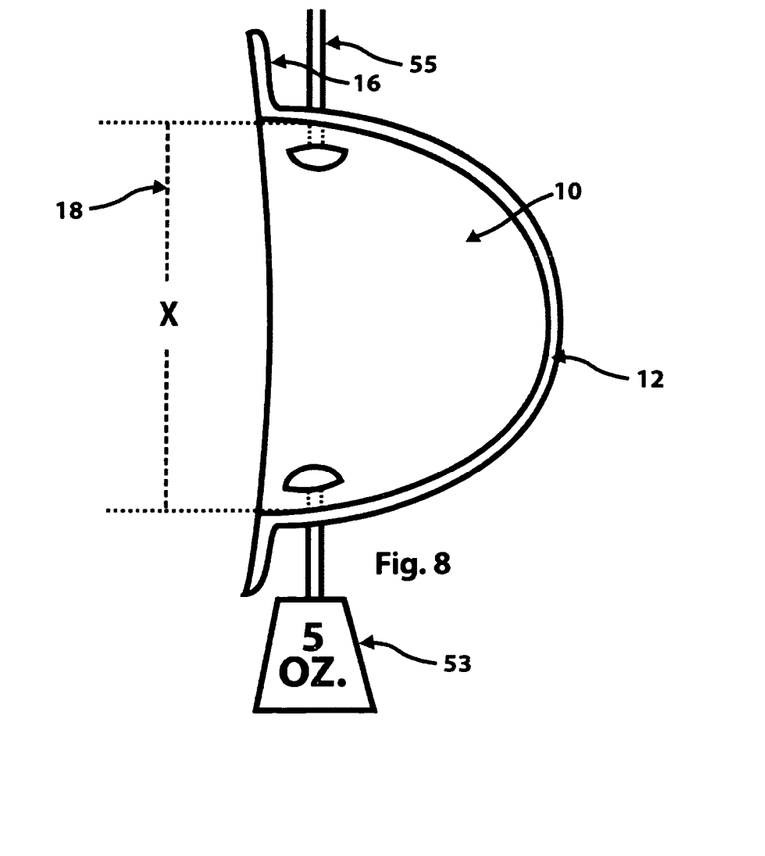
FIG. 8 is a view of the front face of the invention positioned as in FIG. 4, being held in suspension from a fixed point above the invention to a connection on the invention's upper surface and with an object of known weight suspended from the invention's lower surface.
Figure 9:
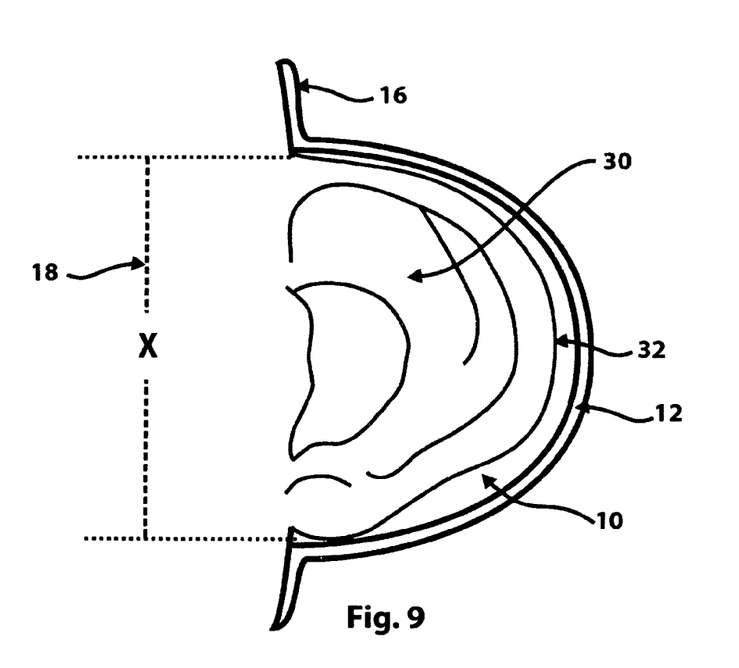
FIG. 9 depicts the invention in use on the user's left ear, as seen with the user looking at the observer, and with the user's external ear held cupped in a forward facing direction by the inner rear face of the invention's pressure against the pinna of the user's ear.
Figure 10:
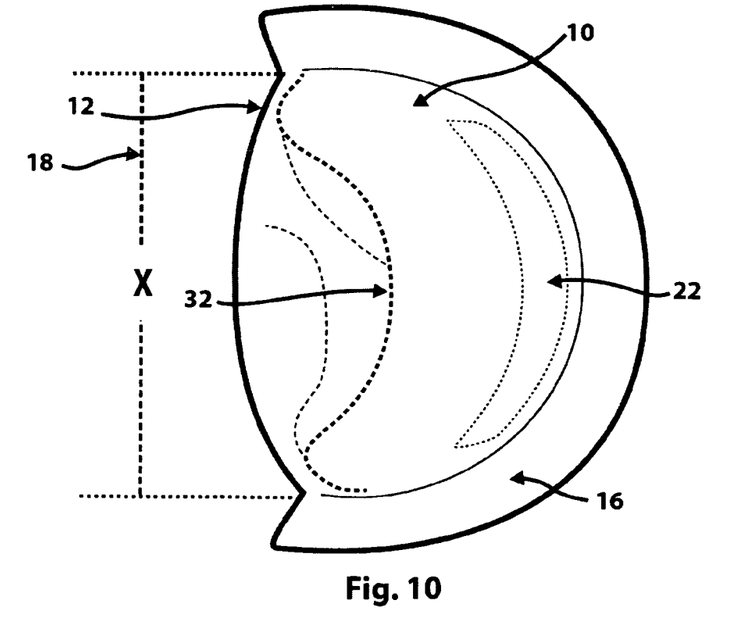
FIG. 10 depicts the invention in use on the user's left ear as seen with the user facing to the left, and as in FIG. 9 with the user's external ear held cupped in a forward facing direction by the invention's pressure against the outer surface of the pinna of the user's ear and fixed in this position by the adhesive strip seen on the inner face of the invention.

We turn now to the drawings on a descriptive basis, with similar reference characters denoting similar elements in all of the several views. FIGS. 1 through 2 illustrate an oblate spherical lune or diangle shaped paraboloid acoustic reflector 10 formed of a relatively thin plastic film as it would appear from the side and above when worn on a user's left ear, with all of the objects located inside the reflector shown with dotted outlines, and with the optional adhesive strip 22 and its protective covering strip 23 shown on the back side of the interior of the reflector 10. FIGS. 3 through 6 illustrate the acoustic reflector 10 as it would appear when not being worn by a user, shown without and with the optional interior adhesive strip 22, from both the outside facing left and from the front. FIGS. 7 through 8 illustrate a means whereby the amount of inward pressure against the top and bottom of the pinna 32 of a prospective wearer that is needed to produce the amount of outward pressure that will force the outer edge 12 of the lens to be deflected to an optimum diameter "X" 18 can be determined. FIGS. 9 through 10 illustrate the lens being worn by a user in which the diameter "X" 18 of the front opening of the lens has been forced outward by the pinna 32 of the wearer to an optimum degree, in which the curve formed by the wall of the lens forms an appropriately parabolic arc.

Figure 11:
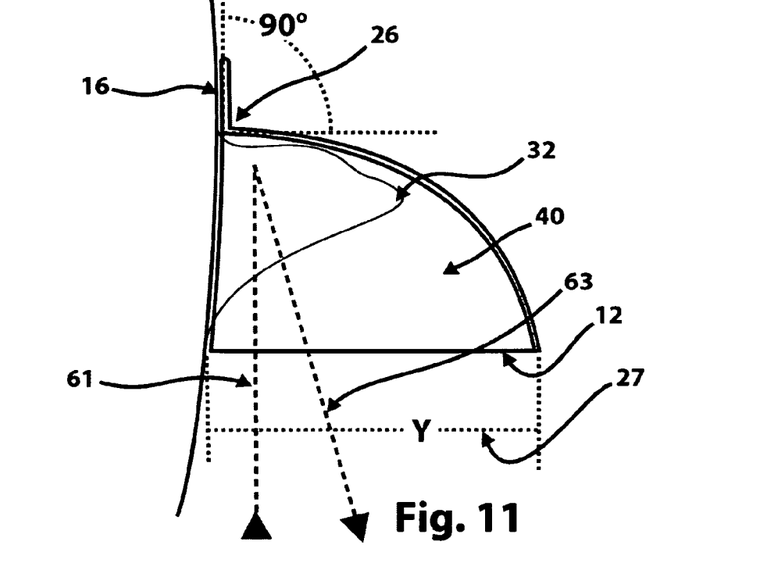
FIG. 11 depicts a conventional passive amplifier acoustic lens made of rigid plastic worn on the left ear of a user as viewed from above; the path of a portion of a sound wave that has originated to the user's front is shown.

FIGS. 10 through 11 compare and contrast the manners in which the parabolic arc of a conventional acoustic ear-mounted lens 40 and the novel lens 10 described in the subject invention reflect sound waves 61 away from 63 or into 65 the ear canal of a wearer of each type of lens. It should be noted that width of the frontal opening "Y"—27—of the conventional lens is greater than the frontal opening "<Y"—29—of the subject invention, due to the need in the case of the subject invention to hold the pinna 32 of the user's ear cupped into a forward-leaning lens shape. This smaller width opening 29 also helps to reduce the visibility of the reflector 10 to outside observers.

Figure 13:
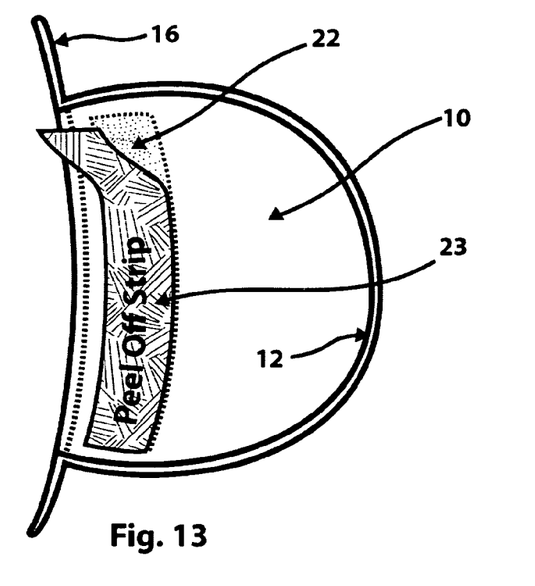
FIG. 13 depicts the invention positioned as in FIG. 5, with the adhesive strip partially covered by a colored strip of removable protective material that has been partially lifted off of the upper portion of the adhesive strip.
Figure 14:
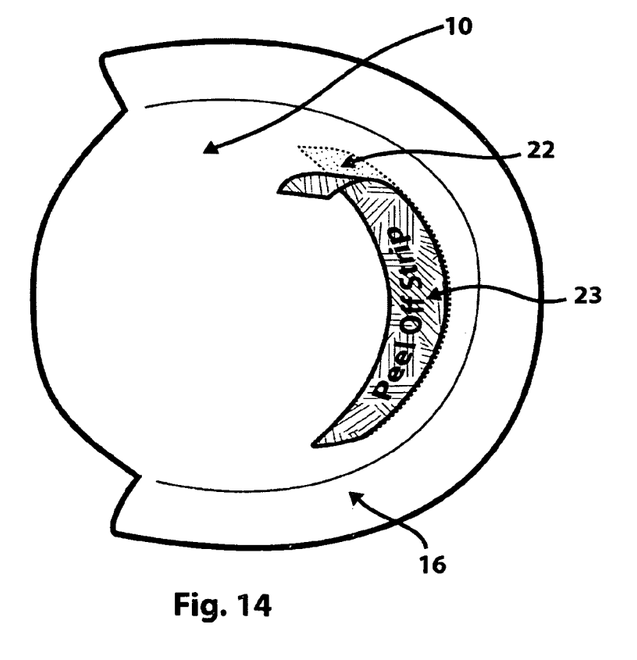
FIG. 14 depicts the invention positioned as in FIG. 6, and as in FIG. 13 with the colored strip of removable material used to protect the adhesive material partially lifted off of the upper portion of the adhesive strip.

FIG. 13 and FIG. 14 depict the manner in which the adhesive-protective covering strip 23 can be made visible to the user by means of coloration, markings, or imprinted instructions in order to assure that the adhesive strip 22 is properly exposed by removal of the protective strip 23 prior to the user's placement of the reflector 10 over the ear.

Figure 12:
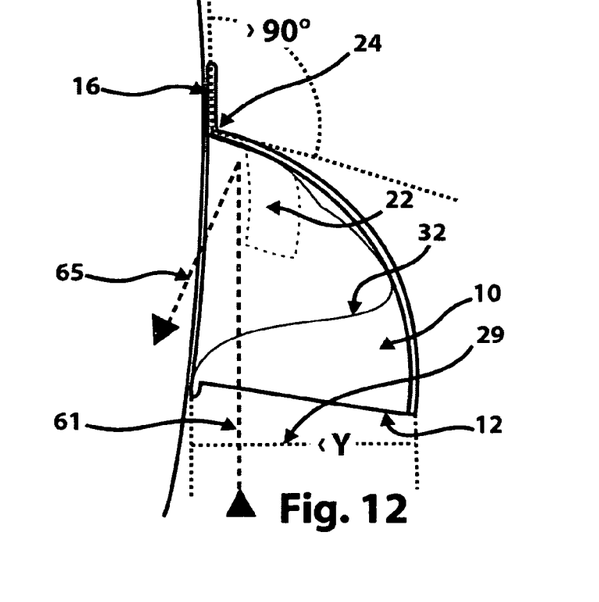
FIG. 12 depicts the invention positioned in the same way as the passive amplifier acoustic lens shown in FIG. 11, worn on the left ear of a user as viewed from above; this depiction reveals the different path taken by the same sound wave that has originated to the user's front as shown in FIG. 11.

As illustrated in FIG. 12, each acoustic reflector 10 is molded out of a moderately flexible plastic film material that, when worn, takes the shape of an oblate spherical lune or diangle shaped paraboloid acoustic reflector that reflects sound radiation to a focal point within the ear canal of the user. In order to permit the acoustic reflector 10 to be passively held in place by the pinna 32 of the user, the flexible plastic film is formed so that the inner face of the reflector 10 cups the rear portion of the user's pinna 32 into a forward-leaning position 32. To insure that the reflector's shape when worn by a user accurately forms an oblate spherical lune or diangle shaped paraboloid of the desired shape as shown in FIGS. 1 and 2, the flexible material of the reflector 10 will be molded so as to form a more tightly curved shape when not worn by a user as shown in FIGS. 3 through 6.

The ideal shape of the reflector shown in FIGS. 1, 2, 7 and 8 is produced when the amount of inward force generated by the distortion of the shape of the reflector 10 is balanced by the equal outward force generated by the material of the pinna 32, particularly its elastic cartilage and collagen fiber contents. At an optimum force and pressure level, such as the five ounces of measured pressure 51 and weights 53 suspended from the base of a top-suspended 55 reflector as illustrated in FIGS. 7 and 8, the proper diameter "X"—18—will be produced between the upper and lower edges of the frontal opening of the reflector 10. Accordingly, the tightly curved shape that the reflector 10 takes when it is not worn as shown in FIGS. 3 through 6 will result in the diameter of the opening between the upper and lower edges of the frontal opening of the reflector being less than distance "X" 18.

To insure the comfort of the user, the inside edge 24 of the lens shape of the oblate spherical lune or diangle shaped paraboloid acoustic reflector 10 that lies against the head of the user will be splayed outward into a semicircular apron shape 16. This same apron shape 16 will provide additional dimensional stability to the reflector 10 as it is purposefully deformed into the desired lens shape when the user places the reflector 10 over the pinna 32 of the ear.

In order to collect the greatest possible amount of sound 61 radiated from a sound source that the user chooses to face as shown in FIG. 7, the angle 24 formed between the arc of the acoustic reflector 10 where it meets the head of the user and the shape of the head of the user outside of the reflector 10 should be obtuse, that is, greater than 90° (>ninety degrees).

This will cause the inner face of the users' pinna 30 to reflect more radiated sound 65 into the ear canal of the user. Prior acoustic lenses used a right angle 26 or acute angle at the intersection of the arc of the reflector 10 and the head of the user external to the acoustic lens 40. This smaller-sized angle 26 had the effect of causing the inner face of the users' pinna 30 to reflect a significant portion of the radiated sound 61 away from the ear canal 63.

In order to assure that the inward pressure of the shape of the reflector 10 is sufficient to hold it in the correct position on the users' ear or ears, the inner face of the reflector 10 can be fitted with an adhesive strip 22 as shown in FIGS. 1, 2, 5 and 6. This strip can be affixed to the back side of the user's pinna 32 when the reflector 10 is properly positioned in a manner that pushes the outer edge of the user's pinna 32 forward to the greatest position comfortably possible as shown in FIG. 12. To protect and preserve the capability of this adhesive strip 22 to adhere to the pinna 32 prior to use, this adhesive can be protected by a strip of removable film material 23 prior to use. In order to assure that the user removes this protective material 23 from the adhesive strip 22 prior to affixing the reflector 10 to the pinna 32, the protective film material 23 can be brightly colored or imprinted with a texture, or with text instructing the user to remove the material 23 before the reflector 10 is placed over their ear.

The nature of the improvements embodied in this invention mechanically simplify and improve the performance of prior art, in the interests of economy of cost, greater fidelity, and broader utility. It is understood that its novel features, as shown and as described in the annexed claims, can be changed in its details of operation and configuration by those skilled in the art without departing from the essence of the invention.

It should further be apparent to those skilled in the art that various changes in form and details of the invention as shown and described may be made. It is intended that such changes be included within the spirit and scope of the claims appended hereto.

I claim:

1. An acoustic device which can be circumferentially mounted over a user's ear and held in place by the inward pressure created by the shape of the device, having a circumference smaller than that of a user's external ear, the device formed of moderately flexible material, the deformation thereof causing the internal pressure against the resisting outward force generated by the device's inward deformation of the external ear of the user, so that:
   a. the parabolic front-facing opening of said device permits sound wave radiation to enter the device where it mechanically reflects into the ear canal of the user greater amounts of these sound waves generated by sound sources faced by the user by means of reshaping and moving forward the pinna of the external ear of the user into a position that permits more of the frontal area of the pinna to reflect these sound waves into the ear canal;
   b. the combined shape of the interior surface of the user's concha and pinna and the inner face of the device phase-coherently concentrate these sound waves and direct them into the user's ear canal by more closely approximating the shape of an oblate spherical lune or diangle paraboloid;
   c. all linear sections of the rear portion at the junction of the lune or diangle paraboloid to the head of the wearer form an obtuse angle.

2. An acoustic device as described in claim 1, wherein said acoustic reflector is further secured to a desired position that is more firmly fixed to the ear of a user by means of a narrow adhesive strip affixed to the inner face of the lune shape of the device with its long axis in a line adjacent to the rim of the device and the base of the pinna of the user.

3. An acoustic device as described in claim 2, wherein the adhesive strip is protected from exposure to contaminants that might diminish the adhesive's capability to adhere to the ear of the user prior to its use by means of a strip of flexible, removable material which covers the adhesive, and which material provides visual cues to the user which clearly indicate that this protective material must be peeled off and discarded prior to use in order to assure the most effective result from use of the acoustic device.

* * * * *